United States Patent [19]

Michaelis

[11] 4,303,578
[45] Dec. 1, 1981

[54] ORGANO-ANTIMONY COMPOUNDS

[75] Inventor: Klaus-Peter Michaelis, Lindenfels, Fed. Rep. of Germany

[73] Assignee: Ciba-Geigy Corporation, Ardsley, N.Y.

[21] Appl. No.: 134,725

[22] Filed: Mar. 27, 1980

[30] Foreign Application Priority Data

Apr. 3, 1979 [CH] Switzerland .......................... 3091/79

[51] Int. Cl.³ .............................................. C08K 5/59
[52] U.S. Cl. .............................. 260/45.75 B; 260/446; 260/410
[58] Field of Search .................. 260/446, 410, 45.75 B

[56] References Cited

U.S. PATENT DOCUMENTS

| | | | |
|---|---|---|---|
| 2,680,726 | 6/1954 | Weinberg et al. | 260/446 X |
| 3,317,576 | 5/1967 | Malz et al. | 260/45.75 B |
| 3,466,261 | 9/1969 | Mauz | 260/45.75 B |
| 4,115,352 | 9/1978 | Boken | 260/45.75 B |

*Primary Examiner*—Helen M. S. Sneed
*Attorney, Agent, or Firm*—Harry Falber

[57] ABSTRACT

Organo-antimony compounds of the formula I

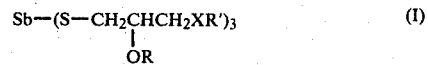

wherein R is hydrogen or $C_1$–$C_{18}$acyl, R' is $C_1$–$C_{20}$alkyl or $C_1$–$C_{18}$acyl, and X is sulfur or oxygen. The compounds are stabilizers for halogen-containing polymers.

9 Claims, No Drawings

ORGANO-ANTIMONY COMPOUNDS

The present invention relates to novel organo-antimony compounds, processes for their production, their use as stabilisers for halogen-containing polymers, and the polymers stabilised therewith.

Organo-antimony compounds are known as stabilisers for PVC. However, these known organo-antimony stabilisers do not always satisfy the requirements of actual practice, especially as regard shelf-life, odourlessness, processing properties at elevated temperature, heat resistance, as well as in special formulations, as e.g. a batch for test samples.

It is the object of the present invention to avoid these disadvantages of the prior art and to provide stabilisers which do not have them or which have them only to a lesser extent.

Accordingly, the invention provides organo-antimony compounds of the formula I

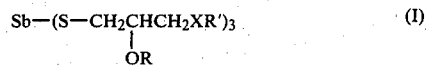

wherein R is hydrogen or $C_1$-$C_{18}$acyl, R' is $C_1$-$C_{20}$alkyl or $C_1$-$C_{18}$acyl, and X is sulfur or oxygen.

R and R' as $C_1$-$C_{18}$acyl are preferably $C_1$-$C_{18}$alkanoyl, $C_7$-$C_{11}$aroyl or also $C_4$-$C_{18}$alkoxycarbonylalkanoyl, such as benzoyl, tert-butylbenzoyl, a ($C_1$-$C_8$alkyl)-maleic acid hemiester, such as methylmaleic acid hemiester, or especially acetyl or propionyl. However, a preferred identity of R as acyl is also acetoacetyl. Each of the radicals R and R' is independent of the other, whilst R' as acyl is in particular also alkanoyl of longer chain length, such as $C_8$-$C_{18}$alkanoyl, e.g. dodecanoyl or especially decanoyl.

X can be oxygen or sulfur, but is preferably oxygen.

R' as $C_1$-$C_{20}$alkyl is straight-chain or especially branched and is preferably $C_8$-$C_{20}$alkyl, such as dodecyl, tetradecyl or octadecyl. Branched radicals are especially preferred, in particular iso-octyl.

Accordingly, preferred compounds are those of the formula I wherein R is $C_1$-$C_{18}$alkanoyl or acetoacetyl, R' is $C_8$-$C_{20}$alkyl or $C_8$-$C_{18}$alkanoyl, and X is oxygen.

Especially preferred compounds are those of the formula I wherein R is acetyl, propionyl or acetoacetyl, R' is $C_8$-$C_{20}$alkyl or $C_8$-$C_{18}$alkanoyl, and X is oxygen.

The most preferred compounds are those of the formula I wherein R is acetyl, propionyl or acetoacetyl, R' is alkyl of 8, 10, 12, 14, 16 or 18 carbon atoms, or is alkanoyl of 8, 10, 12 or 18 carbon atoms, and X is oxygen, as well as the compounds specified in the Examples herein.

The compounds of the formula I can be obtained by methods which are known per se, e.g. by reacting an antimony halide, especially antimony trichloride, with a monothioglycerol ester of the formula II

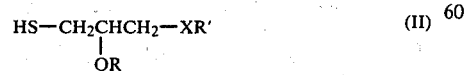

wherein R, R' and X are as defined above. The reaction is preferably carried out in a solvent, especially a halogenated hydrocarbon, such as chloroform, advantageously in the presence of an acid acceptor, such as sodium bicarbonate, and with heating. The water of reaction is removed in a water separator and the solvent is expediently removed by evaporation.

The stabilisers of the present invention are most suitable for protecting chlorinated thermoplastics against heat- and light-induced degradation. Compounds of the formula I are incorporated in the plastics material as a rule in amounts of 0.01 to 10% by weight, preferably 0.1 to 5% by weight. Accordingly, the invention also relates to thermoplastic moulding compositions containing 0.01 to 10% by weight of a stabiliser of the formula I, based on the thermoplastic mixture.

Examples of chlorinated thermoplastics are: polyvinylidene chloride, post-chlorinated polyolefins, and, preferably, polymers of or based on vinyl chloride, e.g. E-, S- and M-PVC, which can also be plasticised and post-chlorinated. A preferred chlorinated thermoplastic, however, is rigid PVC, from which e.g. finished parts for exterior use can be obtained by known methods such as injection moulding or extrusion.

Examples of comonomers for thermoplastics based on vinyl chloride are: vinylidene chloride, trans-dichloroethane, ethylene, propylene, butylene, maleic acid, acrylic acid, fumaric acid, itaconic acid, or vinyl acetate.

Depending on the end use, further additives can be added to the moulding composition before, during or after the addition of the stabiliser. Examples of such additives are: lubricants, preferably montan waxes or glycerol esters, fillers, reinforcing fillers such as glass fibres, and modifiers, such as impact strength additives.

The invention is illustrated in more detail by the following Examples, in which parts and percentages are by weight.

EXAMPLE 1

5 g of solid sodium hydrogen sulfide monohydrate are saturated with hydrogen sulfide at room temperature in 250 ml of methanol. Then 186 g (1 mole) of 2-ethylhexyl glycidyl ether are added dropwise at room temperature and with efficient stirring in the course of 2 hours, while simultaneously introducing hydrogen sulfide gas. The flow of hydrogen sulfide gas is constantly introduced in an amount just sufficient for the reaction solution to take up. The temperature should not exceed 30°-40° C. in order effectively to prevent the formation of corresponding thioethers. When the reaction of the epoxide is complete, the catalyst is destroyed with a small amount of dilute sulfuric acid and the reaction mixture is extracted with ether. The ethereal extract is washed neutral with water, dried over magnesium sulfate and the solvent is removed. Distillation of the residue at 75° C./$10^{-3}$ torr yields the pure monothioglycerol 2-ethylhexyl ether with a SH content of 14.8%.

EXAMPLE 2

In accordance with the conditions of Example 1, 228 g (1 mole) of "CARDURA-E-10" epoxide

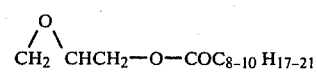

can be reacted in 250 ml of methanol with 5 g of sodium hydrogen sulfide monohydrate as catalyst and hydrogen sulfide for 1½ hours to give the corresponding monothioglycerol monoester. The product can be distilled at 110° C./$10^{-2}$ torr. SH content: 13.4%.

EXAMPLE 3

1 mole of the monothioglycerol ether obtained in Example 1 is diluted with 110 g of acetic anhydride. While cooling with ice-water, 15 ml of conc. sulfuric acid are added dropwise to this solution. The temperature should not exceed 40° C. The batch is stirred for 1 hour, diluted with water, and then extracted with ether. The ethereal extract is washed neutral with sodium bicarbonate solution. Distillation at 85° C./$4.10^{-3}$ torr yields the thioglycerol ester as an odourless oil with a SH content of 11.6%.

EXAMPLE 4

As described in Example 3, the monothioglycerol ether is reacted with propionic anhydride to produce the corresponding propionic acid ester. The odourless product has a SH content of 10.8%.

EXAMPLE 5

220 g of the thioglycerol ether of Example 1 are reacted with 200 ml of ethyl acetate and the mixture is heated until a total amount of 50 ml of ethanol are distilled off. Non-reacted ethyl acetate is then removed in a water jet vacuum, affording in quantitative yield the acetoacetylated thioglycerol ether in the form of a colourless and odourless compound with a SH content of 9.8%.

EXAMPLE 6

262 g of the thioglycerol monoester obtained in Example 2 are reacted with acetic anhydride in accordance with the procedure of Example 3. The resultant thioglycerol diester can be distilled at 120° C./$10^{-3}$ torr and is a completely odourless mercaptan with a SH content of 9.8%.

EXAMPLE 7

260 g of the thioglycerol monoester of Example 2 are reacted with propionic anhydride in accordance with the procedure of Example 4. The thioglycerol diester is also completely odourless and has a SH content of 9.8%.

EXAMPLE 8

260 g of the thioglycerol monoester of Example 2 are reacted with ethyl acetate in accordance with the procedure of Example 5. The acetoacetylated product is a completely odourless mercaptan with a SH content of 8.9%.

Final Products

EXAMPLE 9

The thioglycerol derivatives described in Examples 1 to 8 can be converted into organo-antimony compounds by the following general procedure: 76 g (¼ mole) of antimony trichloride are dissolved with 1 mole of mercaptan in 200 ml of chloroform. To this solution is added 1 mole of sodium bicarbonate as acid acceptor. The mixture is then heated and the water of reaction is drawn off in a water separator. After cooling, sodium chloride is removed by filtration and the solvent is removed in vacuo. The resultant antimony mercaptides are odourless, viscous fluids. Their properties are reported in the following table.

| | Structural formula | $n_D^{20}$ | IR Sb—S | NMR* | Properties |
|---|---|---|---|---|---|
| a | Sb—(SCH$_2$CH(OH)CH$_2$O—CH$_2$CH(CH$_2$CH$_3$)CH$_2$CH$_2$CH$_2$CH$_3$)$_3$ | 1.5248 | 755 | ident. | colourless, odourless and viscous fluid |
| b | Sb—(SCH$_2$CH(OH)CH$_2$O—COC$_{8-10}$H$_{17-21}$)$_3$ | 1.5199 | 755 | ident. | colourless, odourless and viscous fluid |
| c | Sb—(SCH$_2$CHCH$_2$O—CH$_2$CH(CH$_2$CH$_3$)CH$_2$CH$_2$CH$_2$CH$_3$)$_3$ <br>         │ <br>       OCOCH$_3$ | 1.5088 | 755 | ident. | colourless, odourless and viscous fluid |
| d | Sb—(SCH$_2$CHCH$_2$O—CH$_2$CH(CH$_2$CH$_3$)CH$_2$CH$_2$CH$_2$CH$_3$)$_3$ <br>         │ <br>       OCOCH$_2$CH$_3$ | 1.5128 | 755 | ident. | colourless, odourless and viscous fluid |
| e | Sb—(SCH$_2$CHCH$_2$O—CH$_2$CH(CH$_2$CH$_3$)CH$_2$CH$_2$CH$_2$CH$_3$)$_3$ <br>         │ <br>       OCOCH$_2$COCH$_3$ | 1.4978 | 755 | ident. | colourless, odourless and viscous fluid |
| f | Sb(SCH$_2$CHCH$_2$O—COC$_{8-10}$H$_{17-21}$)$_3$ <br>      │ <br>   OCOCH$_3$ | 1.5020 | 755 | ident. | colourless, odourless and viscous fluid |
| g | Sb—(SCH$_2$CHCH$_2$O—COC$_{8-10}$H$_{17-21}$)$_3$ <br>       │ <br>    OCOCH$_2$CH$_3$ | 1.5127 | 755 | ident. | colourless, odourless and viscous fluid |
| h | Sb—(SCH$_2$CHCH$_2$—O—COC$_{8-10}$H$_{17-21}$)$_3$ <br>       │ <br>    OCOCH$_2$COCH$_3$ | 1.5108 | 755 | ident. | colourless, odourless and viscous fluid |

*NMR spectrum identical with starting mercaptan except for SH proton.

EXAMPLE 10

A batch suitable for the manufacture of test samples had the following composition:

| | |
|---|---|
| S-PVC | 100.0 parts |
| paraffin wax | 0.2 part |
| calcium stearate | 1.0 part |
| organo-tin antimony mercaptide | 0.3 part |

After the compounds were thoroughly mixed, a 1 mm sheet was prepared at 180° C. The discolouration (Yellowness Index) of the sheet was then determined:

| | Yellowness Index |
|---|---|
| without stabiliser | 64.4 |

| -continued | Yellowness Index |
|---|---|
| (iC₈H₁₇OCH₂CHCH₂S)<br>  \|<br>  OH | 11.8 |
| (iC₈H₁₇OCH₂CHCH₂S)₃Sb<br>  \|<br>  OCCH₃<br>  ‖<br>  O | 11.3 |
| (iC₈H₁₇OCH₂CHCH₂S)₃Sb<br>  \|<br>  OCCH₂CCH₃<br>  ‖   ‖<br>  O   O | 14.8 |
| (C₉H₁₉COCH₂CHCH₂S)₃Sb<br>  ‖               \|<br>  O              OH | 10.5 |
| (C₉H₁₉COCH₂CHCH₂S)₃Sb<br>  ‖               \|<br>  O              OCCH₃<br>                  ‖<br>                  O | 11.8 |
| (C₉H₁₉COCH₂CHCH₂S)₃Sb<br>  ‖               \|<br>  O              OCCH₂CCH₃<br>                  ‖   ‖<br>                  O   O | 20.6 |

What is claimed is:

1. An organo-antimony compound of the formula I $$Sb-(S-CH_2CHCH_2XR')_3 \quad (I)$$
$$\qquad\qquad\quad | $$
$$\qquad\qquad\;\, OR$$

wherein R is hydrogen or $C_1$-$C_{18}$acyl, R' is $C_1$-$C_{20}$alkyl or $C_1$-$C_{18}$acyl, and X is sulfur or oxygen.

2. A compound of the formula I according to claim 1, wherein R is $C_1$-$C_{18}$alkanoyl or acetoacetyl, R' is $C_8$-$C_{20}$alkyl or $C_8$-$C_{18}$alkanoyl, and X is oxygen.

3. A compound of the formula I according to claim 1, wherein R is acetyl, propionyl or acetoacetyl, R' is $C_8$-$C_{20}$alkyl or $C_8$-$C_{18}$alkanoyl, and X is oxygen.

4. A compound of the formula I according to claim 1, wherein R is acetyl, propionyl or acetoacetyl, R' is alkyl of 8, 10, 12, 14, 16 or 18 carbon atoms, or alkanoyl of 8, 10, 12 or 18 carbon atoms, and X is oxygen.

5. The compound $$Sb-(SCH_2CH(OH)CH_2O-CH_2CH(CH_2CH_3)CH_2CH_2CH_2CH_3)_3$$

according to claim 1.

6. The compound $$Sb-(SCH_2CH(OH)CH_2O-COC_{8-10}H_{17-21})_3$$

according to claim 1.

7. The compound $$Sb-(SCH_2CHCH_2-O-COC_{8-10}H_{17-21})_3$$
$$\qquad\qquad\quad | $$
$$\qquad\qquad OCOCH_2COCH_3$$

according to claim 1.

8. A method of stabilizing chlorinated polymers which comprises incorporating into said polymer an effective stabilizing amount of a compound of the formula I according to any of claims 1 to 7.

9. A chlorinated polymer stabilized with an effective stabilizing amount of a compound according to any of claims 1 to 7.

* * * * *